United States Patent
Tajima et al.

(10) Patent No.: US 10,434,043 B2
(45) Date of Patent: Oct. 8, 2019

(54) WATER-IN-OIL EMULSION SOLID COSMETIC

(71) Applicant: SHISEIDO COMPANY, LTD., Chuo-Ku, Tokyo (JP)

(72) Inventors: Shoji Tajima, Yokohama (JP); Tomoko Ikeda, Yokohama (JP)

(73) Assignee: SHISEIDO COMPANY, LTD., Tokyo (JP)

(*) Notice: Subject to any disclaimer, the term of this patent is extended or adjusted under 35 U.S.C. 154(b) by 0 days.

(21) Appl. No.: 15/118,583

(22) PCT Filed: Oct. 26, 2015

(86) PCT No.: PCT/JP2015/005353
§ 371 (c)(1),
(2) Date: Aug. 12, 2016

(87) PCT Pub. No.: WO2016/017188
PCT Pub. Date: Feb. 4, 2016

(65) Prior Publication Data
US 2017/0056302 A1 Mar. 2, 2017

(30) Foreign Application Priority Data
Aug. 3, 2015 (JP) .................. 2015-153662

(51) Int. Cl.
| | | |
|---|---|---|
| A61K 8/06 | (2006.01) | |
| A61K 8/25 | (2006.01) | |
| A61K 8/26 | (2006.01) | |
| A61K 8/29 | (2006.01) | |
| A61K 8/31 | (2006.01) | |
| A61K 8/41 | (2006.01) | |
| A61Q 1/02 | (2006.01) | |
| A61Q 1/08 | (2006.01) | |
| A61K 8/58 | (2006.01) | |
| A61K 8/89 | (2006.01) | |
| A61K 8/02 | (2006.01) | |
| A61K 8/92 | (2006.01) | |
| A61K 8/891 | (2006.01) | |
| A61K 8/19 | (2006.01) | |
| A61Q 1/00 | (2006.01) | |

(52) U.S. Cl.
CPC ............ *A61K 8/064* (2013.01); *A61K 8/0241* (2013.01); *A61K 8/19* (2013.01); *A61K 8/25* (2013.01); *A61K 8/26* (2013.01); *A61K 8/29* (2013.01); *A61K 8/31* (2013.01); *A61K 8/416* (2013.01); *A61K 8/585* (2013.01); *A61K 8/891* (2013.01); *A61K 8/922* (2013.01); *A61K 8/927* (2013.01); *A61Q 1/00* (2013.01); *A61Q 1/02* (2013.01); *A61Q 1/08* (2013.01)

(58) Field of Classification Search
CPC ... A61K 8/25; A61K 8/26; A61K 8/29; A61K 8/31; A61K 8/416; A61K 8/585; A61K 8/891; A61K 8/927; A61K 8/0241; A61K 8/064; A61K 8/19; A61K 8/922; A61Q 1/02; A61Q 1/08; A61Q 1/00
See application file for complete search history.

(56) References Cited

U.S. PATENT DOCUMENTS

| | | |
|---|---|---|
| 7,037,511 B1 | 5/2006 | Beiersdorfag |
| 2007/0231287 A1 | 10/2007 | Lu |
| 2014/0018444 A1* | 1/2014 | Kitajima ............... A61K 8/375 514/785 |
| 2016/0324758 A1 | 11/2016 | Perrin |

FOREIGN PATENT DOCUMENTS

| | | |
|---|---|---|
| JP | H10330223 | 12/1998 |
| JP | 2009137900 | 6/2009 |
| JP | A 2009-137900 | 6/2009 |
| JP | 2013-107865 | 6/2013 |
| JP | 2013-227295 | 11/2013 |
| WO | WO2015/101729 | 7/2015 |

OTHER PUBLICATIONS

Eng. Translation of JP 2009127900 A, 2009.*
Eng. Translation of JP 2013107865 A, 2013.*
PCT/JP2015/005353, International Search Report and Written Opinion dated Jul. 1, 2016, 7 pages—English.
EP 15827149-1114, European Search Report, dated Dec. 14, 2018, 6 pages—English.

* cited by examiner

*Primary Examiner* — Blessing M Fubara
(74) *Attorney, Agent, or Firm* — Andrew F. Young, Esq.; Lackenbach Siegel, LLP

(57) ABSTRACT

The present invention provides a water-in-oil emulsion solid cosmetic that is further improved in terms of an excellent feeling in use (good spreadability and fresh feeling (texture)) obtained by incorporating a powder in a water phase, and that also has sufficient covering ability, stability even at high temperature, and long-lasting property. The present invention provides a water-in-oil emulsion solid cosmetic comprising an external oil phase comprising a liquid oil thickened or solidified with (A) wax and (B) distearidimonium hectorite, and an internal water phase comprising (C) an internal phase powder dispersed in an aqueous medium.

6 Claims, No Drawings

WATER-IN-OIL EMULSION SOLID COSMETIC

CROSS REFERENCE TO RELATED APPLICATIONS

This application relates to and claims priority from PCT Ser. No. PCT/JP2015/005353 filed Oct. 26, 2015, the entire contents of which are incorporated herein by reference, which in turn claims priority from JP Ser. No. JP2015-153662 filed Aug. 3, 2015.

FIGURE SELECTED FOR PUBLICATION

None

BACKGROUND OF THE INVENTION

Field of the Invention

The present invention relates to a water-in-oil emulsion solid cosmetic. More specifically, the present invention relates to a solid makeup cosmetic that has an improved feeling in use by stably incorporating a powder into an internal water phase and is excellent in stability particularly at high temperatures.

Description of the Related Art

Water-in-oil emulsion-type solid cosmetics are characterized by, for example, being excellent in water resistance as compared with oil-in-water emulsion-type, and being able to efficiently contain an emollient oil, an oil-soluble agent, an ultraviolet absorber, or the like, but may offer a poor refreshing feeling and stickiness or an oily feeling in use. Conventional water-in-oil emulsion solid cosmetics, particularly, makeup cosmetics, are generally produced by dispersing a hydrophobized powder such as a hydrophobized pigment into an oil phase and solidifying the oil phase with a solid wax or the like. Aggregation may, therefore, occur due to the adsorption of powder particles onto the wax. Further problems caused by this aggregate are poor spreadability upon application and reduced freshness. In addition, the hydrophobizing treatment of a powder such as a pigment reduces the oil absorption ability of the powder. Thus, makeup deterioration or damage caused by sebum is difficult to prevent sufficiently.

Patent literature 1 describes a cosmetic having an improved feeling in use such as a refreshing feeling and the absence of stickiness, the cosmetic stably containing 30% by weight or more of water in a water-in-oil-type solid cosmetic by combining (a) long-chain alkyl/polyoxyalkylene-co-modified organosiloxane having an HLB value of 8 or lower and (b) an alkyl group-containing polyoxyalkylene-added nonionic surfactant having an HLB value of 12 or higher. The oil phase, however, contains a hydrophobized pigment powder as a pigment for a makeup cosmetic such as a foundation, an eyeshadow color, or a blusher (Examples 5 to 7), and a base cream and a lip color containing a pigment powder in a water phase have a powder content of 5% by weight at the most (Examples 4 and 8).

Patent literature 2 describes a water-in-oil solid emulsion cosmetic comprising an external oil phase solidified with a wax and/or a gelling agent and states that a cosmetic that has good spreadability upon application, fresh feeling and long-lasting property is obtained by incorporating a powder dispersant which stably disperses a powder in a water phase. The cosmetic specifically described in patent literature 2, however, contains only either one of the wax and the gelling agent, and lacks stability particularly at high temperatures.

In addition, the cosmetics described in patent literatures 1 and 2 each contain a large amount of cyclic silicone oil and therefore there are problems associated with feeling in use, such as poor spreadability and reduced refreshing feeling.

CITATION LIST

Patent Literature

[PTL 1] JP-A-H10-330223
[PTL 2] JP-A-2009-137900

ASPECTS AND SUMMARY OF THE INVENTION

Technical Problem

Accordingly, the problem to be solved by the present invention is to provide a water-in-oil emulsion solid cosmetic that is further improved in terms of an excellent feeling in use (good spreadability and fresh feeling (texture)) obtained by incorporating a powder in a water phase, and that also has sufficient covering ability, stability even at high temperature, and long-lasting property.

Solution to Problem

The present inventors have diligently studied to attain the above object and consequently completed the present invention based on findings not only that a non-hydrophobized powder can stably incorporated into a water phase but also that stability at high temperature can be further improved by solidifying the oil phase with a wax and disteardimonium hectorite in a water-in-oil emulsion-type solid cosmetic containing a powder dispersed in an internal water phase.

More specifically, the present invention provides a water-in-oil emulsion solid cosmetic comprising an external oil phase comprising a liquid oil thickened or solidified with (A) a wax and (B) disteardimonium hectorite, and an internal water phase comprising (C) an internal phase powder dispersed in an aqueous medium.

Advantageous Effects of Invention

The water-in-oil emulsion solid cosmetic of the present invention contains a non-surface-hydrophobized powder in a water phase. The water-in-oil emulsion solid cosmetic of the present invention therefore has good spreadability upon application to the skin and offers a fresh feeling (texture). In addition, the water-in-oil emulsion solid cosmetic of the present invention is also excellent in oil absorption ability and has long-lasting property. Furthermore, the water-in-oil emulsion solid cosmetic of the present invention comprises an oil phase thickened or solidified with a wax and disteardimonium hectorite and is therefore excellent in stability particularly at high temperatures.

The fresh feeling (texture) upon application obtainable by the solid cosmetic of the present invention is such a fresh, juicy and unique feeling (texture) as if lots of internal water is poured out by the collapse of a solid cosmetic upon applying the solid cosmetic to the skin.

The above and other aspects, features and advantages of the present invention will become apparent from the following description read in conjunction with the accompanying drawings, in which like reference numerals designate the same elements.

BRIEF DESCRIPTION OF THE DRAWINGS

None

DETAILED DESCRIPTION OF THE PREFERRED EMBODIMENTS

Reference will now be made in detail to embodiments of the invention. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

DESCRIPTION OF EMBODIMENTS

The essential features of the water-in-oil emulsion solid cosmetic of the present invention are that: an external oil phase is thickened or solidified with (A) a wax and (B) disteardimonium hectorite; and a non-hydrophobized powder (internal phase powder) is stably dispersed and contained in an internal water phase.

Hereinafter, each component constituting the water-in-oil emulsion solid cosmetic (hereinafter, also simply referred to as a "solid cosmetic") of the present invention will be described in detail.

The external oil phase in the solid cosmetic according to the present invention is thickened or solidified with (A) a wax and (B) disteardimonium hectorite.

The wax (component A) used in the present invention can be selected from waxes conventionally used in makeup cosmetics.

Specific examples thereof include: solid oils and fats such as cacao butter, coconut oil, horse oil, hydrogenated coconut oil, palm oil, beef tallow, mutton tallow, and hydrogenated castor oil; hydrocarbons such as paraffin wax (linear hydrocarbon), microcrystalline wax (branched saturated hydrocarbon), ceresin wax, Japan wax, montan wax, and Fischer-Tropsch wax; waxes such as beeswax, lanolin, carnauba wax, candelilla wax, rice bran wax (rice wax), spermaceti, jojoba oil, bran wax, montan wax, kapok wax, bayberry wax, shellac wax, sugarcane wax, lanolin fatty acid isopropyl, hexyl laurate, reduced lanolin, hard lanolin, POE lanolin alcohol ether, POE lanolin alcohol acetate, POE cholesterol ether, lanolin fatty acid polyethylene glycol, and POE hydrogenated lanolin alcohol ether, higher fatty acids such as myristic acid, palmitic acid, stearic acid, and behenic acid; and higher alcohols such as cetyl alcohol, stearyl alcohol, behenyl alcohol, myristyl alcohol, and cetostearyl alcohol. These may be used singly or in combinations of two or more.

Among them, paraffin wax (linear hydrocarbon), microcrystalline wax (branched saturated hydrocarbon), ceresin wax, and jojoba oil are preferably used.

The content of (A) wax in the solid cosmetic of the present invention is an amount in which the wax can thicken or solidify the oil phase together with (B) disteardimonium hectorite mentioned below to form the solid cosmetic. The content is usually 0.1 to 30% by mass, preferably 1 to 25% by mass, more preferably 2 to 20% by mass, further preferably 3 to 15% by mass.

The disteardimonium hectorite (component B) in the present invention is one type of organic modified clay mineral conventionally used as an oil phase thickener (gelling agent) for cosmetics or the like. For example, disteardimonium hectorite commercially available under the trade name of "Bentone® 38V" or "Bentone® 38VCG" (Elements Specialities, Inc.) can be preferably used.

The content of the disteardimonium hectorite in the solid cosmetic of the present invention is 0.05 to 2.5% by mass, preferably 0.1 to 2% by mass, more preferably 0.25 to 1% by mass.

The content ratio of (A) wax to (B) disteardimonium hectorite (A/B=wax/disteardimonium hectorite) is preferably set to a range of 1 to 200.

In the external oil phase in the solid cosmetic of the present invention, liquid oil is thickened or solidified with (A) wax and (B) disteardimonium hectorite.

In the present specification, the "liquid oil" means an oil that is in a liquid state at normal temperature (25° C.) and may usually be used in cosmetics and pharmaceuticals.

The liquid oil constituting the solid cosmetic of the present invention preferably comprises a liquid silicone oil. The liquid silicone oil includes a volatile or nonvolatile linear silicone oil and cyclic silicone oil. In the present specification, the linear silicone oil includes silicone oils having a linear or branched chain structure. Specific examples thereof include dimethylpolysiloxane, methylphenylpolysiloxane, and methyl hydrogen polysiloxane. Examples of the cyclic silicone oil include decamethylcyclopentasiloxane, dodecamethylcyclohexasiloxane, and octamethylcyclotetrasiloxane.

In conventional oil-type or water-in-oil emulsion-type solid cosmetics, a silicone oil is routinely used as a liquid oil constituting an external oil phase. Particularly, a volatile cyclic silicone oil is contained in many cases. A cyclic silicone incorporated in a emulsion improves stability, but may adversely affect a feeling in use. Since the solid cosmetic of the present invention attains excellent stability by incorporating (A) wax and (B) disteardimonium hectorite, the content of the cyclic silicone oil can be decreased, and therefore certain possible aspect of the present invention is free from cyclic silicone oil. For example, in the solid cosmetic of the present invention, the content ratio of a cyclic silicone oil to a linear silicone oil (cyclic silicone oil/linear silicone oil) can be set to 0 to 3.0, preferably 0 to 2.0, more preferably 0 to 1.0.

In addition to the aforementioned silicone oil or instead of the silicone oil, a non-silicone oil such as a hydrocarbon oil or an ester oil can be used as the liquid oil.

Specific examples of the non-silicone oil include: liquid oils and fats such as avocado oil, camellia oil, macadamia nut oil, mink oil, olive oil, castor oil, jojoba oil, triglycerin, and glycerin trioctanoate; hydrocarbons such as liquid paraffin, squalane, paraffin, ceresin, and squalene; higher fatty acids such as lauric acid, myristic acid, palmitic acid, stearic acid, behenic acid, oleic acid, 12-hydroxystearic acid, isostearic acid, linoleic acid, and linolenic acid; higher alcohols such as lauryl alcohol, cetyl alcohol, stearyl alcohol, behenyl alcohol, oleyl alcohol, monostearyl glycerol ether, monopalmityl glycerol ether, cholesterol, phytosterol, and isostearyl alcohol; and ester oils such as isononyl isononanoate, isopropyl myristate, cetyl octanoate, octyldodecyl myristate, butyl stearate, decyl oleate, ethylene glycol dioctanoate, diisostearyl malate, trimethylolpropane trioctanoate, trimethylolpropane triisostearate, pentaerythritol tetraoctanoate, glycerin trioctanoate, glycerin triisostearate, ethyl acetate, butyl acetate, and amyl acetate. These may be used singly or in combinations of two or more.

The content of the liquid oil in the solid cosmetic of the present invention is generally set to preferably 20 to 70% by mass. The ratio of the liquid oil to the whole oil phase components solidified with (A) wax and (B) disteardimonium hectorite is preferably set to 50 to 97% by mass.

Besides, the silicone oil preferably occupies 50% by mass or more, 60% by mass or more, or 70% by mass or more of the liquid oil.

In the internal water phase of the solid cosmetic of the present invention, (C) an internal phase powder is dispersed in an aqueous medium.

In the present specification, the "internal phase powder" means a powder that is a powder with a hydrophilic surface and stably dispersible in an aqueous system and may usually be used in cosmetics and pharmaceuticals. The powder with a hydrophilic surface encompasses a hydrophilic powder without hydrophobizing treatment on its surface or a hydrophobic powder with a hydrophilizing treatment on its surface.

Specific examples of the internal phase powder include: inorganic powders (e.g., talc, kaolin, sericite, muscovite, synthetic mica, phlogopite, lepidolite, biotite, lithia mica, vermiculite, magnesium carbonate, calcium carbonate, diatomaceous earth, magnesium silicate, calcium silicate, aluminum silicate, barium silicate, strontium silicate, tungstic acid metal salt, silica, hydroxyapatite, zeolite, boron nitride, and ceramic powder); inorganic white pigments (e.g., zinc oxide); inorganic red pigments (e.g., iron titanate); inorganic violet pigments (e.g., mango violet and cobalt violet); inorganic green pigments (e.g., chromium oxide, chromium hydroxide, and cobalt titanate); inorganic blue pigments (e.g., ultramarine and iron blue); pearl pigments (e.g., titanium oxide-coated mica, titanium oxide-coated bismuth oxychloride, titanium oxide-coated talc, colored titanium oxide-coated mica, bismuth oxychloride, and argentine); iron red, yellow oxide of iron, black oxide of iron, and carbon black; metal powder pigments (e.g., aluminum powder and copper powder); organic pigments such as zirconium, barium, or aluminum lake (e.g., organic pigments such as Red No. 201, Red No. 202, Red No. 204, Red No. 205, Red No. 220, Red No. 226, Red No. 228, Red No. 405, Orange No. 203, Orange No. 204, Yellow No, 205, Yellow No. 401, and Blue No. 404, Red No. 3, Red No. 104, Red No. 106, Red No. 227, Red No. 230, Red No. 401, Red No, 505, Orange No. 205, Yellow No. 4, Yellow No. 5, Yellow No. 202, Yellow No. 203. Green No. 3, and Blue No. 1); and natural dyes (e.g., chlorophyll and [□-carotene] β-carotene), These may be used singly or in combinations of two or more.

The content of the internal phase powder in the solid cosmetic of the present invention is 0.1 to 25% by mass, preferably 1 to 15% by mass, more preferably 3 to 12% by mass, with respect to the cosmetic. If the content of the powder component is less than 0.1% by mass, the cosmetic effect due to the powder may become insufficient. If the content exceeds 25% by mass, the powder may aggregate without being sufficiently dispersed in the water phase or may move out from the water phase into the oil phase, thereby causing reduction in feeling in use.

In the internal water phase of the solid cosmetic of the present invention, the aforementioned internal phase powder may be dispersed stably and favorably in the aqueous medium by use of a powder dispersant. In the present specification, the powder dispersant refers to a substance that can be adsorbed onto the surface of a powder component so that the powder component is prevented from aggregating and thereby uniformly dispersed in the aqueous medium.

Examples of the powder dispersant that may be used in the present invention include aqueous dispersants usually used in cosmetics and pharmaceuticals, for example, nonionic surfactants, fatty acid soaps, condensed phosphoric compounds, polycarboxylic compounds (ammonium polycarboxylate, etc.), amino acid compounds, polyacrylic compounds, and amines (amino alcohol, etc.). In the present invention, a nonionic surfactant, a fatty acid soap, and a condensed phosphoric compound are particularly preferably used.

Examples of the nonionic surfactant include hydrophilic surfactants (HLB=8 or higher, preferably 10 or higher) such as: POE-sorbitan fatty acid esters (e.g., POE-sorbitan monooleate, POE-sorbitan monostearate, and POE-sorbitan tetraoleate); POE sorbitol fatty acid esters (e.g., POE-sorbitol monolaurate, POE-sorbitol monooleate, POE-sorbitol pentaoleate, and POE-sorbitol monostearate); POE-glycerin fatty acid esters (e.g., POE-monooleates such as POE-glycerin monostearate, POE-glycerin monoisostearate, and POE-glycerin triisostearate); POE-fatty acid esters (e.g., POE-distearate, POE-monodioleate, and ethylene glycol distearate); Pluronic-type surfactants (e.g., Pluronic); POE/POP-alkyl ethers (e.g., POE/POP-cetyl ether, POE/POP-2-decyl tetradecyl ether, POE/POP-monobutyl ether, POE/POP-hydrogenated lanolin, and POE/POP-glycerin ether); tetra-POE/tetra-POP-ethylenediamine condensates (e.g., Tetronic); POE-castor oil and -hydrogenated castor oil derivatives (e.g., POE-castor oil, POE-hydrogenated castor oil, POE-hydrogenated castor oil monoisostearate, POE-hydrogenated castor oil triisostearate, POE-hydrogenated castor oil monopyroglutamic acid monoisostearic acid diester, and POE-hydrogenated castor oil maleic acid); POE-beeswax/lanolin derivatives (e.g., POE-sorbitol beeswax); alkanolamides (e.g., coconut oil fatty acid diethanolamide, lauric acid monoethanolamide, and fatty acid isopropanolamide); POE-propylene glycol fatty acid esters; POE-alkylamines; POE-fatty acid amides; alkylethoxydimethylamine oxides; and trioleyl phosphate.

Examples of the fatty acid soap include sodium laurate, sodium myristate, sodium palmitate, sodium stearate, potassium laurate, potassium myristate, potassium palmitate, and potassium stearate. The fatty acid such as lauric acid, myristic acid, palmitic acid, and/or stearic acid may be prepared and allow to act as a fatty acid soap during preparation of a water phase by preliminarily incorporating potassium hydroxide or sodium in the water phase and subsequently adding the fatty acid thereto.

Examples of the condensed phosphoric compound include trisodium phosphate, sodium pyrophosphate, and sodium hexametaphosphate.

The content of the powder dispersant can be appropriately adjusted by, for example, the type or the amount of the powder to which the powder dispersant is applied and/or the amount of the water phase components, and is usually set to preferably approximately 0.02 to 5% by mass, more preferably approximately 0.5 to 4% by mass, with respect to the whole cosmetic.

The aqueous medium in which the internal phase powder is dispersed by use of the powder dispersant may be water or a mixture of water and an aqueous solvent, for example, lower alcohol.

The content of the water phase components in the solid cosmetic of the present invention is generally 1 to 70% by mass, preferably 3 to 60% by mass, more preferably 5 to 50% by mass. If the content of the water phase components is lower than 1% by mass, a sufficient amount of the powder cannot be dispersed therein.

The solid cosmetic of the present invention may contain, in addition to the aforementioned indispensable components, other optional components that may be contained in usual solid cosmetics as long as they do not impair the effects of the present invention.

The optional components that are incorporated mainly in the external oil phase include an external phase powder, an oil component, and the like.

In the present specification, the "external phase powder" means a powder as powder listed for examples of the internal phase powder but whose surface is hydrophobizing-treated with silicone, fluorine, Teflon®, a fatty acid, a fatty acid soap, lauroyllysine, or the like, as well as a powder originally having a hydrophobic surface, such as a silicone resin powder, all of which correspond to a powder component that is incorporated in external oil phases in conventional water-in-oil emulsion solid cosmetics.

The solid cosmetic of the present invention stably contains a relatively large amount of the powder (internal phase powder) in the internal water phase and thereby produces a sufficient cosmetic effect. The content of the external phase powder can therefore be significantly decreased, as compared with conventional solid cosmetics.

The content of the external phase powder is 18% by mass or less at the most, preferably 10% by mass or less, more preferably 7% by mass or less. The solid cosmetic of the present invention also encompasses an aspect free from the external phase powder. For improving a makeup finish, it is preferred that the solid cosmetic of the present invention should contain approximately 5 to 7% by mass of the external phase powder.

Examples of the oil component include oil-soluble components other than those described above such as natural or synthetic solid oils or semisolid oils (except for the aforementioned wax), ultraviolet absorbers, fat-soluble vitamins, lecithin, antioxidants, and fragrance.

The ultraviolet absorbers include: benzoic acid ultraviolet absorbers such as p-aminobenzoic acid; anthranilic acid ultraviolet absorbers such as methyl anthranilate; salicylic acid ultraviolet absorbers such as octyl salicylate and phenyl salicylate; cinnamic acid ultraviolet absorbers such as isopropyl p-methoxycinnamate, octyl p-methoxycinnamate, and glyceryl di-p-methoxycinnamate mono-2-ethylhexanoate; benzophenone ultraviolet absorbers such as 2,4-dihydroxybenzophenone, 2-hydroxy-4-methoxybenzophenone, and 2-hydroxy-4-methoxybenzophenone-5-sulfonic acid; oil-soluble ultraviolet absorbers such as 2-(2'-hydroxy-5'-methylphenyl)benzotriazole and 4-tert-butyl-4'-methoxybenzoylmethane.

Examples of the antioxidants include ascorbic acid, α-tocopherol, dibutylhydroxytoluene, and butylhydroxyanisole.

The optional components that are incorporated mainly in the internal water phase include moisturizing agents, water-soluble polymers, sequestering agents, various water-soluble agents, and the like.

Examples of the moisturizing agents include 1,3-butylene glycol, polyethylene glycol, propylene glycol, dipropylene glycol, hexylene glycol, glycerin, diglycerin, xylitol, maltitol, maltose, and D-mannitol.

Examples of the water-soluble polymers include: plant-derived polymers such as gum arabic, carrageenan, pectin, agar, quince seeds (*Pyrus cydonia* seeds), starch, alga colloids (brown alga extracts); microbe-derived polymers such as dextran and pullulan; animal-derived polymers such as collagen, casein, and gelatin; starch polymers such as carboxymethyl starch and methylhydroxypropyl starch; alginic acid polymers such as sodium alginate; vinyl polymers such as carboxyvinyl polymers (CARBOPOL, etc.); polyoxyethylene polymers; polyoxyethylene-polyoxypropylene copolymers; acrylic polymers such as sodium polyacrylate and polyacrylamide; and inorganic water-soluble polymers such as bentonite, magnesium aluminum silicate, and Laponite.

Examples of the sequestering agents include sodium edetate, sodium metaphosphate, and phosphoric acid.

Examples of the water-soluble agents include: vitamins such as vitamin A, retinol, retinol palmitate, inositol, pyridoxine hydrochloride, benzyl nicotinate, nicotinic acid amide, DL-α-tocopherol nicotinate, magnesium ascorbyl phosphate, ascorbic acid 2-glucoside, vitamin D2 (ergocalciferol), potassium ascorbyl tocopheryl phosphate, dl-α-tocopherol, dl-α-tocopherol acetate, pantothenic acid, and biotin; anti-inflammatory agents such as allantoin and azulene; whitening agents such as arbutin; astringent agents such as zinc oxide and tannic acid; and sulfur, lysozyme chloride, pyridoxine hydrochloride, and γ-oryzanol.

In the present invention, an emulsifier that may generally be used in water-in-oil emulsion compositions can be used as an emulsifier for emulsifying the aforementioned water phase components in the oil phase components. A hydrophobic emulsifier (HLB=7 or lower) is preferably used as such an emulsifier. Examples thereof include: sorbitan fatty acid esters such as sorbitan monolaurate, sorbitan monooleate, sorbitan monoisostearate, and sorbitan tristearate; glycerol fatty acid esters such as glycerol monostearate, glycerol monooleate, glycerol isostearate, diglycerol diisostearate, and decaglyceryl pentaisostearate; polyoxyethylene hydrogenated castor oils such as POE(5), POE (7.5), or POE(10) hydrogenated castor oils; dipolyhydroxystearic acid esters: high-molecular-weight lipophilic activators such as polyglyceryl-2 dipolyhydroxystearate (manufactured by Cognis Japan Ltd.; PGPH), and PEG30 dipolyhydroxystearate (manufactured by Uniqema Ltd.; Arlacel P135); polyether silicones such as cetyl dimethicone copolyol [e.g., "ABIL EM90" (manufactured by Evonik Goldschmidt GmbH)], polyether-modified silicone [e.g., "KF6017" (manufactured by Shin-Etsu Chemical Co., Ltd.)], and cross-linked polyether-modified silicone [e.g., "KSG" series (manufactured by Shin-Etsu Chemical Co., Ltd.)]; and polyglycerin silicones such as polyglycerin-modified silicone and alkyl/polyglycerin-comodified silicone. In the present invention, one or more of these emulsifiers having HLB of 7 or lower can be used. Particularly, a polyether or polyglycerin silicone emulsifier is preferably used.

The optional components in the solid cosmetic of the present invention are not limited to those described above. Other optional components that may be incorporated in cosmetics can be used in the internal water phase or the external oil phase as long as they do not impair the effects of the present invention.

The term "solid" or "solid state" used herein is understood as a meaning usually used in the cosmetic field and can be defined as, for example, a form or a state in which the whole composition does not exhibit flowability at a temperature of 50° C. or lower and does not exhibit significant deformation under ordinary storage conditions, The solid cosmetic of the present invention is suitable for being provided as a makeup cosmetic such as a foundation, an eyeshadow, an eyeliner, a mascara, or a blusher, and particularly, as a solid foundation. The solid cosmetic of the present invention can also be provided as a make-up base or a sunscreen.

The solid cosmetic of the present invention can be produced through the steps of: mixing with optionally heating water phase components, and mixing a powder therewith; and separately mixing with optionally heating oil phase components including a wax and/or a gelling agent, and then emulsifying the water phase components containing the powder dispersed therein in the resulting oil phase components.

Specifically, the solid cosmetic of the present invention can be produced by the following procedures:

(1) An internal phase powder is added into a mixed solution of water phase components, and resultant is stirred and mixed using a homomixer or the like to obtain a powder dispersion (water phase). In the case of adding a powder dispersant, the powder dispersant is added into the mixed solution.

(2) Subsequently, the dispersion (water phase) and, optionally, an emulsifier are added to a mixture of oil phase components including a wax and disteardimonium hectorite and a liquid oil which are appropriately dissolved by heating in advance, and the resultant mixture is stirred and mixed using a homomixer or the like to prepare an emulsion.

(3) Finally, the emulsion is appropriately filled into a container and solidified by cooling to obtain the solid cosmetic of the present invention.

EXAMPLES

Hereinafter, the present invention will be described in more detail with reference to Examples. However, the present invention is not intended to be limited by them by any means. Each content is indicated by % by mass with respect to a system containing the components, unless otherwise specified.

Each water-in-oil emulsion solid foundation was prepared according to the procedure described in the paragraph 0039 using the composition listed in the tables given below.

The obtained solid foundation was evaluated for (1) stability at high temperatures and (2) good (light) spreadability and freshness in practical use tests as follow:

Evaluation Methods (1) High-Temperature Stability

The sample of each example was stored at 80° C. for 1 to 2 hours. Then, each sample was visually observed and evaluated according to the following criteria:

A: The emulsion was stable, and no change was seen in its appearance,

B: The emulsion had a homogeneous surface but exhibited slight separation (or aggregation) in the inside (which was not a problem in practical use), C: Separation was observed in whole emulsion.

(2) Practical Use Test (Good Spreadability and Freshness)

The sample of each example was applied to the cheeks of 20 expert panelists and evaluated according to the following criteria:

A: 18 or more of 20 panelists said that the sample was well spreadable or fresh.

B: 8 to 17 of 20 panelists said that the sample was well spreadable or fresh.

C: 7 or less of the 20 panelists said that the sample was well spreadable or fresh.

TABLE 1

|  | Comparative Example 1 | Example 1 | Example 2 | Example 3 | Example 4 | Comparative Example 2 |
|---|---|---|---|---|---|---|
| Dimethylipolysiloxane | 41.55 | 41.5 | 41.3 | 41.05 | 40.55 | 38.55 |
| Decamethylcyclopentasiloxane | — | — | — | — | — | — |
| Polyoxyethylene hydrogenated castor oil (60) | 0.45 | 0.45 | 0.45 | 0.45 | 0.45 | 0.45 |
| Glycerin | 3 | 3 | 3 | 3 | 3 | 3 |
| 1,3-Butylene glycol | 5 | 5 | 5 | 5 | 5 | 5 |
| Internal phase powder lake[1] | 4 | 4 | 4 | 4 | 4 | 4 |
| (B) Disteardimonium hectorite | — | 0.05 | 0.25 | 0.5 | 1 | 3 |
| PEG-10 dimethicone | 2 | 2 | 2 | 2 | 2 | 2 |
| (A) Microcrystalline wax | 4 | 4 | 4 | 4 | 4 | 4 |
| (A) Paraffin wax | 5 | 5 | 5 | 5 | 5 | 5 |
| Ion-exchanged water | 35 | 35 | 35 | 35 | 35 | 35 |
| High-temperature stability | C | B | B | A | A | A |
| Spreadability | A | A | A | A | A | C |
| Freshness | A | A | A | A | A | C |
| A/B | — | 180 | 36 | 18 | 9 | 3 |

[1]The internal phase powder lake contained a mixture of 0.7 parts of talc, 4.5 parts of titanium oxide, 0.59 parts of yellow oxide of iron, 0.2 parts of red oxide of iron, and 0.01 parts of black oxide of iron.

TABLE 2

|  | Example 1 | Example 5 | Example 6 | Comparative Example 3 | Example 2 | Example 7 | Example 8 | Comparative Example 4 |
|---|---|---|---|---|---|---|---|---|
| Dimethylpolysiloxane | 41.5 | 36.5 | 26.5 | 21.5 | 41.3 | 35.3 | 30.3 | 15.3 |
| Decamethylcyclopentasiloxane | — | — | — | — | — | — | — | — |
| Polyoxyethylene hydrogenated castor oil (60) | 0.45 | 0.45 | 0.45 | 0.45 | 0.45 | 0.45 | 0.45 | 0.45 |
| Glycerin | 3 | 3 | 3 | 3 | 3 | 3 | 3 | 3 |
| 1,3-Butylene glycol | 5 | 5 | 5 | 5 | 5 | 5 | 5 | 5 |
| Internal phase powder lake[1] | 4 | 4 | 4 | 4 | 4 | 10 | 15 | 30 |
| External phase powder[2] | — | 5 | 15 | 20 | — | — | — | — |

TABLE 2-continued

|  | Example 1 | Example 5 | Example 6 | Comparative Example 3 | Example 2 | Example 7 | Example 8 | Comparative Example 4 |
|---|---|---|---|---|---|---|---|---|
| (B) Disteardimonium hectorite | 0.05 | 0.05 | 0.05 | 0.05 | 0.25 | 0.25 | 0.25 | 0.25 |
| PEG-10 dimethicone | 2 | 2 | 2 | 2 | 2 | 2 | 2 | 2 |
| (A) Microcrystalline wax | 4 | 4 | 4 | 4 | 4 | 4 | 4 | 4 |
| (A) Paraffin wax | 5 | 5 | 5 | 5 | 5 | 5 | 5 | 5 |
| Ion-exchanged water | 35 | 35 | 35 | 35 | 35 | 35 | 35 | 35 |
| High-temperature stability | B | B | B | B | B | B | B | C |
| Spreadability | A | A | B | C | A | A | A | B |
| Freshness | A | A | B | C | A | A | A | B |
| A/B | 180 | 180 | 180 | 180 | 36 | 36 | 36 | 36 |

*[1])The internal phase powder lake contained a mixture of 0.7 parts of talc, 4.5 parts of titanium oxide, 0.59 parts of yellow oxide of iron, 0.2 parts of red oxide of iron, and 0.01 parts of black oxide of iron.
*[2])The external phase powder was a polymethylsilsesquioxane powder.

TABLE 3

|  | Example 1 | Example 9 | Example 10 | Example 11 | Example 2 | Example 12 |
|---|---|---|---|---|---|---|
| Dimethylpolysiloxane | 41.5 | 11.5 | 21.5 | 45.3 | 41.3 | 35.3 |
| Decamethylcyclopentasiloxane | — | 30 | 20 | — | — | — |
| Polyoxyethylene hydrogenated castor oil (60) | 0.45 | 0.45 | 0.45 | 0.45 | 0.45 | 0.45 |
| Glycerin | 3 | 3 | 3 | 3 | 3 | 3 |
| 1,3-Butylene glycol | 5 | 5 | 5 | 5 | 5 | 5 |
| Internal phase powder lake*[1]) | 4 | 4 | 4 | 4 | 4 | 4 |
| (B) Disteardimonium hectorite | 0.05 | 0.05 | 0.05 | 0.25 | 0.25 | 0.25 |
| PEG-10 dimethicone | 2 | 2 | 2 | 2 | 2 | 2 |
| (A) Microcrystalline wax | 4 | 4 | 4 | 2 | 4 | 7 |
| (A) Paraffin wax | 5 | 5 | 5 | 3 | 5 | 8 |
| Ion-exchanged water | 35 | 35 | 35 | 35 | 35 | 35 |
| High-temperature stability | B | B | B | B | B | B |
| Spreadability | A | B | B | A | A | B |
| Freshness | A | B | B | A | A | B |
| A/B | 180 | 180 | 180 | 20 | 36 | 60 |

*[1])The internal phase powder lake contained a mixture of 0.7 parts of talc, 4.5 parts of titanium oxide, 0.59 parts of yellow oxide of iron, 0.2 parts of red oxide of iron, and 0.01 parts of black oxide of iron.

TABLE 4

|  | Example 4 | Comparative Example 5 | Comparative Example 6 | Comparative Example 7 |
|---|---|---|---|---|
| Dimethylpolysiloxane | 40.55 | 40.55 | 40.55 | 40.55 |
| Decamethylcyclopentasiloxane | — | — | — | — |
| Polyoxyethylene hydrogenated castor oil (60) | 0.45 | 0.45 | 0.45 | 0.45 |
| Glycerin | 3 | 3 | 3 | 3 |
| 1,3-Butylene glycol | 5 | 5 | 5 | 5 |
| Internal phase powder lake*[1]) | 4 | 4 | 4 | 4 |
| Disteardimonium hectorite | 1 | — | — | — |
| (Dimethicone/vinyl dimethicone) crosspolymer | — | 1 | — | — |
| 12-Hydroxystearic acid | — | — | 1 | — |
| Dextrin fatty acid ester | — | — | — | 1 |
| PEG-10 dimethicone | 2 | 2 | 2 | 2 |
| Microcrystalline wax | 4 | 4 | 4 | 4 |
| Paraffin wax | 5 | 5 | 5 | 5 |
| Ion-exchanged water | 35 | 35 | 35 | 35 |
| High-temperature stability | A | C | C | Not solidified |
| Spreadability | A | A | A |  |
| Freshness | A | A | A |  |

*[1])The internal phase powder lake contained a mixture of 0.7 parts of talc, 4.5 parts of titanium oxide, 0.59 parts of yellow oxide of iron, 0.2 parts of red oxide of iron, and 0.01 parts of black oxide of iron.

As is evident from the results shown in Table 1, the samples each having an external oil phase comprising a liquid oil thickened or solidified with 0.05% by mass or more and 2.5% by mass or less of disteardimonium hectorite and a wax in combination were excellent in stability at high temperatures, good spreadability, and freshness. By contrast, the sample of Comparative Example 1 containing no disteardimonium hectorite was inferior in high-temperature stability, and the sample of Comparative Example 2 having a disteardimonium hectorite content exceeding 2.5% by mass produced neither good spreadability nor freshness.

As seen from the results shown in Table 2 (left columns), the sample of Example 1 containing no external phase powder and the samples of Examples 5 and 6 having an external phase powder content of 18% by mass or less achieved satisfactory outcomes in all properties, whereas the sample of Comparative Example 3 having an external phase powder content exceeding 18% by mass had poor spreadability and poor freshness. As seen from the results shown in Table 2 (right columns), the samples of Examples 2, 7, and 8 having an internal phase powder content of 25% by mass or less achieved satisfactory outcomes in all properties, whereas an internal phase powder content exceeding 25% by mass was shown to reduce stability at high temperatures (Comparative Example 4).

The results shown in Table 3 (left columns) demonstrated that favorable properties were obtained even when a portion of a linear silicone oil was replaced with a volatile cyclic silicone oil. The results shown in Table 3 (right columns) demonstrated that satisfactory properties were obtained even when the amount of the wax was changed.

As seen from the results shown in Table 4, gelling agents other than disteardimonium hectorite was unable to achieve stabilization at high temperatures even if those gelling agents are routinely used in cosmetics. In particular, the dextrin fatty acid ester was unable to solidify the oil phase even if the same amount of the wax was contained.

Hereinafter, Formulation Examples of the water-in-oil solid emulsion cosmetic according to the present invention will be given. However, the present invention is not intended to be limited by them.

Formulation Example 1: Solid Emulsion Foundation

| (Ingredients) | (% by mass) |
|---|---|
| (1) dimethylpolysiloxane | 27.8 |
| (2) decamethylcyclopentasiloxane | 10 |
| (3) microcrystalline wax | 3 |
| (4) paraffin wax | 6 |
| (5) nylon-12 | 3 |
| (6) octyl methoxycinnamate | 3 |
| (7) isononyl isononanoate | 3 |
| (8) PEG-10 dimethicone | 2 |
| (9) disteardimonium hectorite | 0.5 |
| (10) internal phase powder lake | 6 |
| (11) ion-exchanged water | 30 |
| (12) 1,3-butylene glycol | 2 |
| (13) glycerin | 3 |
| (14) trisodium phosphate | 0.5 |
| (15) antiseptic | 0.1 |
| (16) flavor | 0.1 |

(Production Method)

(i) The internal phase powder (10) was added into a mixed solution of the water phase components (11) to (15), and this mixture was stirred and mixed using a homomixer or the like to obtain a powder dispersion (water phase).

(ii) Subsequently, the dispersion (water phase) and, optionally, an emulsifier were added to a mixture of the components (1) to (9) appropriately dissolved by heating and (16), and this mixture was stirred and mixed using a homomixer or the like to prepare an emulsion.

(iii) Finally, the emulsion was appropriately filled into a container and solidified by cooling to obtain the solid emulsion foundation of this Formulation Example.

The internal phase powder lake contained a mixture of 0.7 parts of talc, 4.5 parts of titanium oxide, 0.59 parts of yellow oxide of iron, 0.2 parts of red oxide of iron, and 0.01 parts of black oxide of iron.

Formulation Example 2: Emulsion Blusher

| (Ingredients) | (% by mass) |
|---|---|
| (1) dimethylpolysiloxane | 43.6 |
| (2) microcrystalline wax | 1 |
| (3) ceresin wax | 5 |
| (4) sorbitan monoisostearate | 1 |
| (5) (vinyl dimethicone/methicone silsesquioxane) crosspolymer | 1 |
| (6) PEG-10 dimethicone | 2 |
| (7) disteardimonium hectorite | 0.7 |
| (8) internal phase powder lake | 4 |
| (9) ion-exchanged water | 35 |
| (10) propylene glycol | 6 |
| (11) polyoxyethylene glycerin monoisostearate | 0.5 |
| (12) antiseptic | 0.1 |
| (13) flavor | 0.1 |

(Production Method)

After mixing of the components (9) to (12), the component (8) was added to the mixture and dispersed therein, Next, a mixture of the components (1) to (7) and (13) preheated to 80° C. was added to this mixture and emulsified and dispersed therein. Then, the resulting mixture was filled into an inside plate in a flowable state and cooled to room temperature to obtain the emulsion blusher of this Formulation Example.

The internal phase powder lake contained a mixture of 0.5 parts of talc, 2.8 parts of titanium oxide, and 0.7 parts of red oxide of iron.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A water-in-oil emulsion solid cosmetic, comprising:
   an external oil phase comprising a liquid oil thickened or solidified with (A) wax and (B) disteardimonium hectorite; and
   an internal water phase comprising (C) 0.1 to 25% by mass of an internal phase powder with a hydrophilic surface dispersed in an aqueous medium;
   wherein the liquid oil comprises a silicone oil; and
   wherein the silicone oil contains a linear silicone oil and is free from cyclic silicone oil.

2. The cosmetic according to claim 1, further comprising:
   a powder dispersant which disperses the internal phase powder, wherein the powder dispersant is one or more dispersants selected from the group consisting of a nonionic surfactant, a fatty acid soap, and a condensed phosphoric compound.

3. The cosmetic, according to claim 2, wherein:
   the external oil phase further comprises 5 to 18% by mass of an external phase powder.

4. The cosmetic, according to claim 1, wherein:
the external oil phase further comprises 5 to 18% by mass or less of an external phase powder.

5. The cosmetic according to claim 1, wherein:
(C) the internal phase powder is one or two or more selected from the group consisting of: talc, kaolin, sericite, muscovite, synthetic mica, phlogopite, lepidolite, biotite, lithia mica, vermiculite, magnesium carbonate, calcium carbonate, diatomaceous earth, magnesium silicate, calcium silicate, aluminum silicate, barium silicate, strontium silicate, tungstic acid metal salt, silica, hydroxyapatite, zeolite, boron nitride, ceramic powder, zinc oxide, iron titanate, mango violet, cobalt violet, chromium oxide, chromium hydroxide, cobalt titanate, ultramarine, iron blue, titanium oxide-coated mica, titanium oxide-coated bismuth oxychloride, titanium oxide-coated talc, colored titanium oxide-coated mica, bismuth oxychloride, argentine, iron red, yellow oxide of iron, black oxide of iron, carbon black, aluminum powder, copper powder, zirconium, barium, aluminum lake, Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404, Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, Blue No. 1, chlorophyll and β-carotene.

6. A water-in-oil emulsion solid cosmetic, comprising:
an external oil phase comprising a liquid oil thickened or solidified with (A) wax and (B) disteardimonium hectorite;
an internal water phase comprising (C) 0.1 to 25% by mass of an internal phase powder with a hydrophilic surface dispersed in an aqueous medium;
wherein the liquid oil comprises a silicone oil;
wherein the silicone oil contains a linear silicone oil and is free from cyclic silicone oil;
a powder dispersant which disperses the internal phase powder, wherein the powder dispersant is one or more dispersants selected from the group consisting of a nonionic surfactant, a fatty acid soap, and a condensed phosphoric compound; and
the external oil phase further comprises 5 to 18% by mass of an external phase powder.

* * * * *